(12) United States Patent
Pedrazzini

(10) Patent No.: US 10,155,631 B2
(45) Date of Patent: Dec. 18, 2018

(54) APPARATUS FOR TRANSFERRING SPECIMENS OF BIOLOGICAL MATERIAL BETWEEN LABORATORY AUTOMATION SYSTEMS PLACED AT DIFFERENT HEIGHTS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 248 days.

(21) Appl. No.: 15/030,987

(22) PCT Filed: Oct. 20, 2014

(86) PCT No.: PCT/IB2014/065468
§ 371 (c)(1),
(2) Date: Apr. 21, 2016

(87) PCT Pub. No.: WO2015/059620
PCT Pub. Date: Apr. 30, 2015

(65) Prior Publication Data
US 2016/0251170 A1    Sep. 1, 2016

(30) Foreign Application Priority Data

Oct. 23, 2013  (IT) .............................. MI2013A1763

(51) Int. Cl.
*B65G 47/57*  (2006.01)
*B65G 17/12*  (2006.01)
(Continued)

(52) U.S. Cl.
CPC ........... *B65G 47/57* (2013.01); *B65G 17/123* (2013.01); *B65G 43/08* (2013.01);
(Continued)

(58) Field of Classification Search
CPC ...... B65G 17/123; B65G 43/08; B65G 47/57; G01N 2035/0406; G01N 2035/0465; G01N 2035/0467; G01N 2035/0484
See application file for complete search history.

(56) References Cited

U.S. PATENT DOCUMENTS 3,184,032 A * 5/1965 Jonsson ................. B65G 17/12
198/463.4
4,465,177 A * 8/1984 Dorner ................... B65G 47/57
198/475.1

(Continued)

FOREIGN PATENT DOCUMENTS

DE  20 2004 013 601    11/2004
EP  0 300 619           1/1989
JP  11264828 A  *      9/1999

OTHER PUBLICATIONS

International Search Report, dated Mar. 30, 2015.
(Continued)

*Primary Examiner* — Gene O Crawford
*Assistant Examiner* — Keith R Campbell
(74) *Attorney, Agent, or Firm* — Jacobson Holman, PLLC.

(57) ABSTRACT

An apparatus for the transfer of conveying devices of containers of biological products between laboratory automation systems placed at different heights. The apparatus include a motor-driven belt arranged transversely with respect to the automation systems. Shelves are fixed to the motor-driven belt for accommodating the conveying devices during the transfer. The conveying devices are loaded/unloaded on/from the shelves of the apparatus by the action of pushers. The belt allows for, by rotation, a simultaneous bidirectional transfer, both in ascent and descent, of conveying devices from one automation system to the other.

5 Claims, 7 Drawing Sheets

(51) Int. Cl.
*B65G 43/08* (2006.01)
*G01N 35/04* (2006.01)

(52) U.S. Cl.
CPC .............. *B65G 2201/0261* (2013.01); *G01N 2035/0406* (2013.01); *G01N 2035/0465* (2013.01); *G01N 2035/0467* (2013.01); *G01N 2035/0484* (2013.01)

(56) References Cited

U.S. PATENT DOCUMENTS

| | | | |
|---|---|---|---|
| 5,224,585 A | 7/1993 | Blanco et al. | |
| 5,351,801 A | 10/1994 | Markin et al. | |
| 5,672,512 A | 9/1997 | Shaw | |
| 7,708,135 B2* | 5/2010 | Ellerth | B65G 47/57 198/797 |
| 8,252,232 B2* | 8/2012 | Neeper | C01N 35/00732 198/468.8 |
| 8,877,128 B2* | 11/2014 | Fukugaki | G01N 35/026 198/346.2 |
| 9,810,706 B2* | 11/2017 | Riether | G01N 35/10 |
| 2009/0107803 A1 | 4/2009 | Ellerth et al. | |
| 2015/0233955 A1* | 8/2015 | Nemoto | G01N 35/04 198/602 |
| 2017/0059599 A1* | 3/2017 | Riether | G01N 35/026 |

OTHER PUBLICATIONS

Written Opinion of the International Searching Authority, dated Mar. 30, 2015.
Italian Patent Application No. MI2013A000181, dated Aug. 2, 2013, with English translation of the claims.

\* cited by examiner

APPARATUS FOR TRANSFERRING SPECIMENS OF BIOLOGICAL MATERIAL BETWEEN LABORATORY AUTOMATION SYSTEMS PLACED AT DIFFERENT HEIGHTS

The present invention relates to an apparatus for the transfer of specimens of biological material between laboratory automation systems placed at different heights.

BACKGROUND OF THE INVENTION

Automation systems for the movement of test tubes in an analysis laboratory have increasingly large dimensions, and now a single laboratory room is often not sufficient to contain the entire system and all analysis modules interfacing therewith.

In most laboratories, multiple automation systems are therefore arranged, separate from one another, in different rooms possibly even located on different floors of the laboratory itself. Each system may be interfaced, according to the space available, with a certain amount of assay modules, also different from one another from system to system.

However, it is frequent the case in which a same specimen is to be taken over and analyzed, in a sequence, by modules that interface with separate automation systems located in different rooms.

The most obvious solution clearly is the pick up of a certain amount of specimens contained in test tubes by an operator and their manual transfer from one room to another, i.e. from one automation system to another. This solution is not very practical, first because it may keep the operator in charge constantly engaged, who could instead carry out other tasks in the laboratory, and it would also be preferable to ensure a supply of specimens to the system where they should be transferred, which occurs immediately when there is a need, regardless of the more or less regular movements, from one room to the other, of the operator as the test tube carrier.

Apparatuses which carry out operations of this kind are already known, for example a transfer of specimens, each contained in a test tube in turn accommodated in a conveying device, from a conveyor of a laboratory automation system to a second conveyor placed at a different height.

However, in the known solutions, the apparatus in question can only operate in an alternating manner, as an elevator at certain times and as a descender at others, as there is only one path available for both the ascent and the descent of conveying devices. Accordingly, if the path is occupied by a conveying device which is for example going up, one must wait for the completion of that operation before a descent operation of a next conveying device may possibly start along the same path.

U.S. Pat. No. 5,672,512 describes a vertical chain conveyor for the transfer of biological material. Said conveyor includes shelves adapted to overturn the biological material from one inlet area to an outlet area located at the same height.

EP-0300619 describes a chain conveyor for the transfer of parcels between locations at different heights. Said conveyor includes reclining shelves for loading and unloading the parcels. In order to load the parcels on the shelves and vice versa, means are required to tilt said shelves and thus the parcels to help them rise on the shelves or vice versa descend from the shelves.

BRIEF SUMMARY OF THE INVENTION

It is the object of the present invention to provide an apparatus with a bidirectional mechanism for the simultaneous ascent and descent of conveying devices containing specimens, thus parallelizing the operations and considerably speeding up, compared to the known solutions, the exchange of specimens between one automation system and the other.

This and other objects are achieved by an apparatus as described in claim 1.

BRIEF DESCRIPTION OF THE SEVERAL VIEWS OF THE DRAWINGS

These and other features of the present invention will become more apparent from the following detailed description of an embodiment thereof, made by way of a non-limiting example with reference to the accompanying drawings, in which.

DETAILED DESCRIPTION OF THE INVENTION

Figure 1:
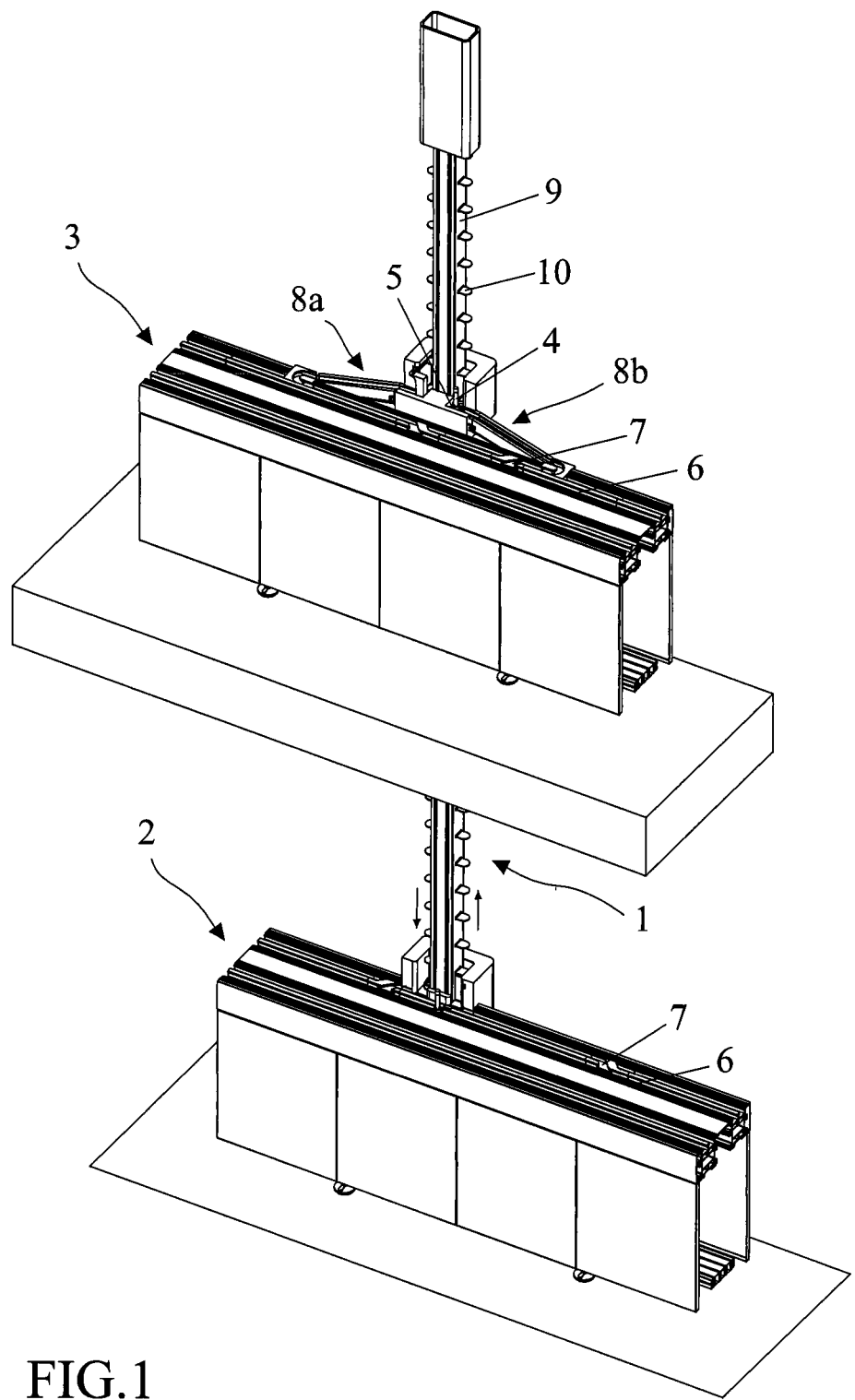
FIG. 1 shows a perspective view of the apparatus according to the invention, interfaced with two laboratory automation systems placed at different heights.
Figure 2:
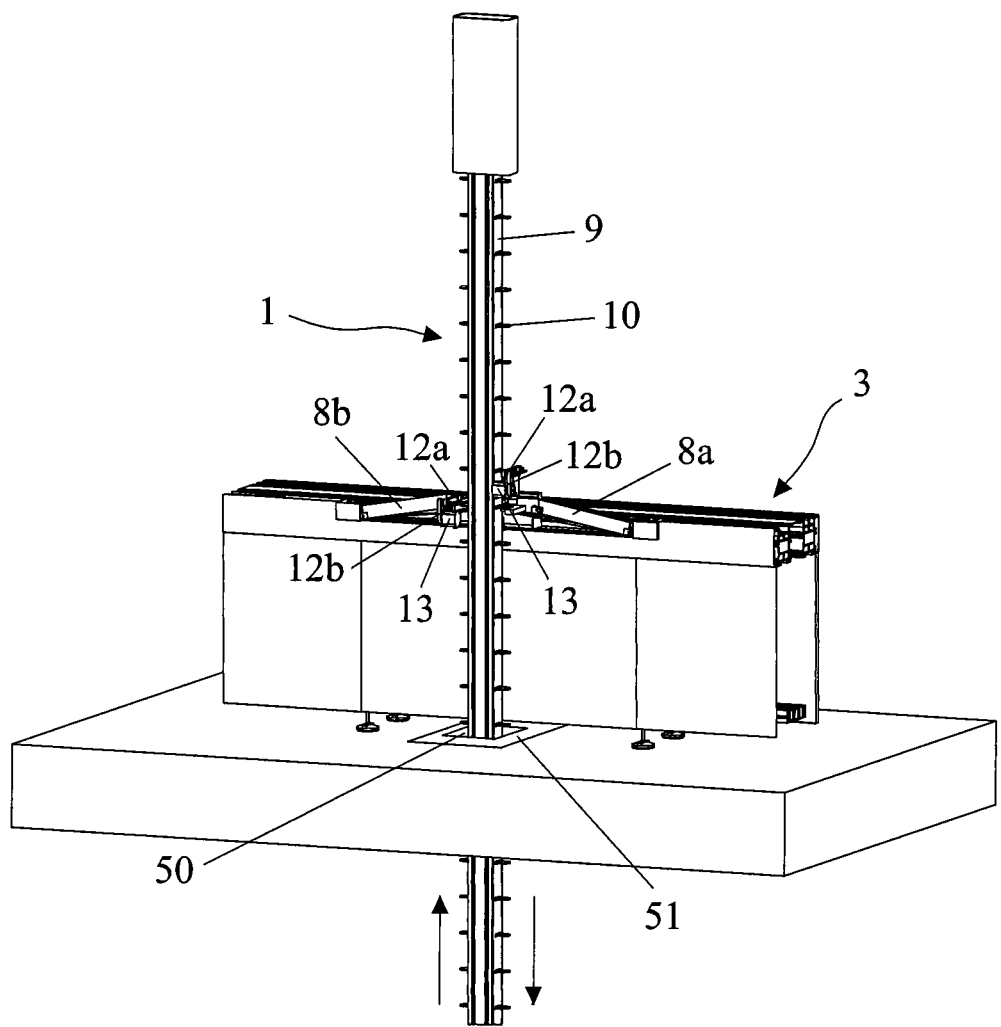
FIG. 2 shows a rear view of a further detail of the interfacing between the apparatus and one of the two automation systems.

An apparatus 1 connects together two different automation systems 2, 3, for example placed in two separate rooms (located one above the other) of an analysis laboratory (FIG. 1). Apparatus 1 extends through both rooms, through a suitable cavity 50 made in the ceiling of the room on the lower floor, and is used to transfer specimens of biological material, contained in test tubes 4, between systems 2 and 3 in both directions. Cavity 50 may be protected by a layer 51 of insulating and fire-retardant material, such as rock wool (FIG. 2).

Each test tube 4 is in turn contained in conveying devices 5 for a single test tube 4, and may indifferently be capped or uncapped. According to the specific needs of the analysis modules connected to systems 2 and 3, the possibility to also transfer empty conveying devices 5 along apparatus 1 may also be included.

Figure 4:
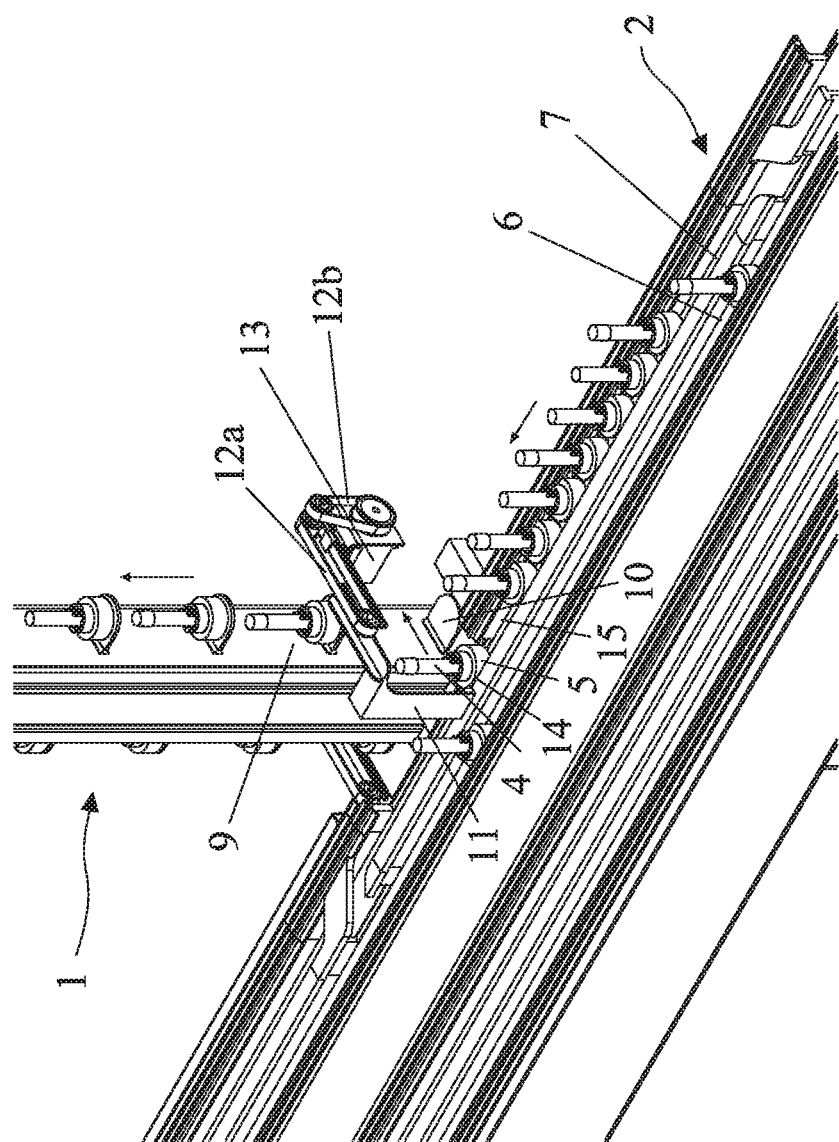
FIG. 4 shows a perspective view of a detail of the step of loading specimens from the automation system, placed at a lower height, to the apparatus.

Each conveying device 5 is adapted to keep the respective test tube 4 in a vertical position, as shown for example in FIG. 4.

The conveying devices 5 which must be directed towards the apparatus 1 in order to be loaded thereon are diverted along the automation system 2 or 3, from a main lane 6 to a secondary lane 7 directly interfaced with apparatus 1. Likewise, during the step of unloading from apparatus 1, the conveying devices 5 are first released along the secondary lane 7 to then return to the main lane 6 and hence resume their path along system 2 or 3 (FIG. 1).

The interfacing between the automation system 3 placed in the room on the upper floor and apparatus 1 is actually accomplished by using two peripheral units (spurs) 8a and 8b with a ramp section (FIG. 1), similar to that described in Italian patent application MI2013A000181 to the Applicant. This is to carry out a fine adjustment and exactly adapt the height of the loading/unloading point of the conveying devices 5 on/from apparatus 1 for every possible height of system 3 relative to the floor of the upper room, and for the extension of every possible height of the ceiling of the lower room; this is required since apparatus 1 moves according to fixed steps, as will be better explained hereafter.

Figure 3:
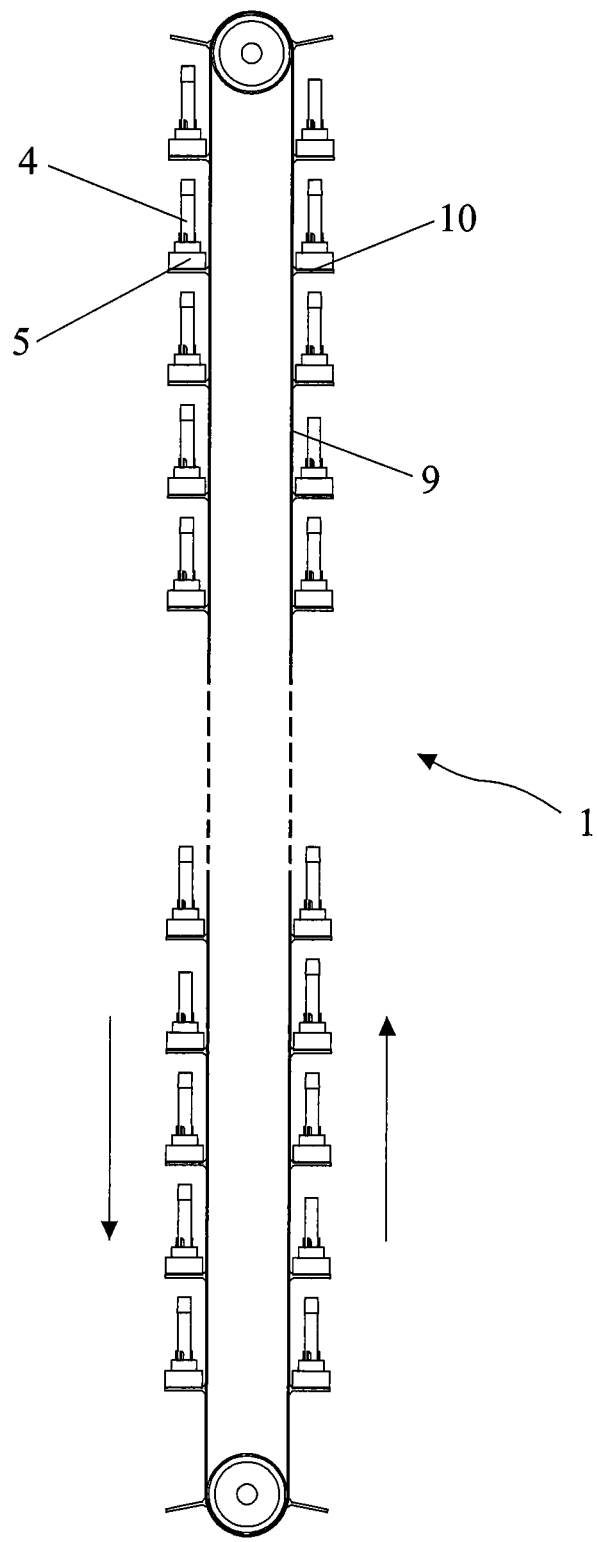
FIG. 3 shows a front view of the apparatus only.

Apparatus 1 comprises a motor-driven belt 9 to which shelves 10 are fixed, at a regular distance from one another and over the entire length thereof, which are intended to receive and transport the conveying devices 5, either empty or with test tube 4, along belt 9 (FIG. 3).

Said shelves 10 are horizontal along the entire transfer path so that the test tubes 4 remain vertically arranged during the height change.

Belt 9 is vertically arranged and, looking frontally at apparatus 1 from the automation system (either the lower 2 or higher 3 system), this causes the effect to have the upward movement of the conveying devices 5 on one side and the downward movement on the opposite side.

Apparatus 1 further comprises pushers 11 (FIGS. 4-7) adapted to carry out the horizontal displacement of the conveying devices 5 from one of the two automation systems 2, 3 to the shelves 10 of apparatus 1, as well as carry out, at the other end of apparatus 1, the opposite operation; in other words, pushers 11 carry out both the start and the completion of the operation of transferring specimens from one automation system 2, 3 to the other.

It is worth noting that, in any case, the peripheral units 8a, 8b have a horizontal section at the transfer zone adjacent to belt 9 so that the translation of the conveying devices 5 is horizontal, thus keeping the test tubes 4 vertical.

It is very important that, in the transfer step, the test tube 4 is kept vertical; the tilting of the test tube 4 could in fact cause the displacement thereof with respect to the conveying device 5 or even an uncoupling from the latter.

Moreover, keeping the test tube 4 vertical allows better preserving the biological material contained therein, thus preventing motions that may alter the biological material itself by unintended mixing, or even cause the escape thereof when the test tube 4 is uncapped, which are all very unpleasant situations especially if the biological material has yet to be analyzed.

The operation of the pushers 11 is ensured by a sliding system thereof, comprising a pair of belts 12a and 12h driven by a motor 13, and sensors 14 which start such a sliding movement only if it is actually needed, i.e. if there actually is a conveying device 5 which must be moved from apparatus 1 to the automation system 2, 3, or vice versa.

Apparatus 1 is therefore designed to ensure a continuous exchange of specimens between two (or possibly more than two) automation systems 2, 3 vertically placed on two (or more) distinct levels.

Therefore, assuming that there are conveying devices 5, with or without test tube 4, which are to be transported from system 2 on the lower floor to system 3 on the upper floor, they are suitably diverted (according to a control from a control unit) from the main lane 6 to the secondary lane 7 of the automation system 2 on the lower floor.

Upon the arrival of the diverted conveying device 5 at the interface with apparatus 1, sensor 14 detects the presence of the conveying device 5 and then actuates pusher 11 which moves the transport conveying device 5 from the secondary lane 7 to the shelf 10 of apparatus 1, suitably stopped at the correct height so that shelf 10 is at the same level with system 2 and therefore ready to accommodate the conveying device 5 (FIG. 4).

Multiple conveying devices 5 may be diverted along the secondary lane 7, one after the other; in this case, a queue is formed along the same lane and the actuation of pusher 11 to place multiple conveying devices 5 in a sequence on different consecutive shelves 10 of apparatus 1 is almost continuous, the stepping movement of the latter being perfectly coordinated with the thrust of each conveying device 5 by means of pusher 11.

Obviously, nothing changes if the arrival of the conveying devices 5 at the interface with apparatus 1 is irregular; their release and subsequent conveying to a shelf 10 of apparatus 1 is always handled in a suitable manner, possibly by blocking the conveying device 5 for a certain period of time by means of a stop gate 15 placed at the end of the secondary lane 7. This is to ensure that the release is in any case synchronized with the sliding of the belt 9 of apparatus 1, and thus of the shelves 10 thereof.

The operating principle just described, with reference to the loading of the conveying devices 5 from the automation system 2 placed in the room on the lower floor, is also substantially identical in the other three loading/unloading points that interface with apparatus 1.

Figure 5:
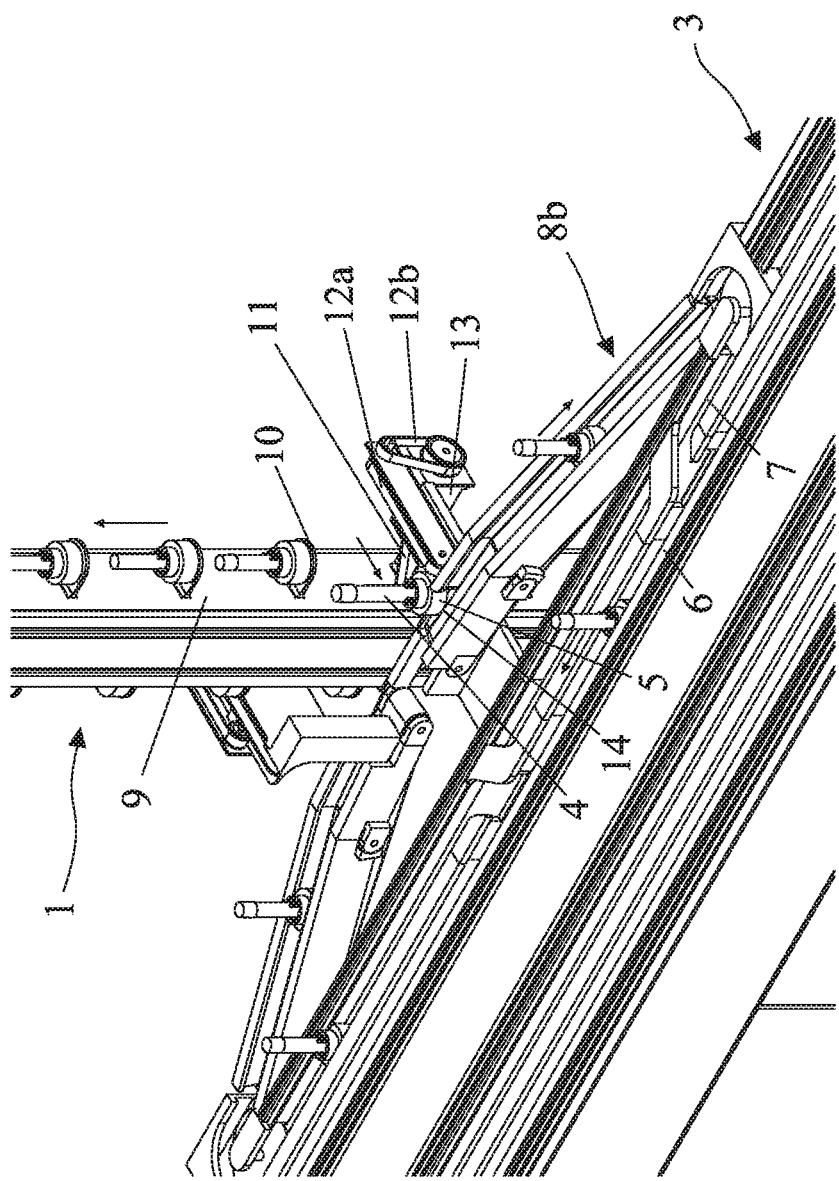
FIG. 5 shows a perspective view of a detail of the step of unloading specimens from the apparatus to the automation system placed at a higher height.

In particular, the conveying devices 5 loaded on apparatus 1 (as described above), once the top of the apparatus itself has been reached, are detected by a sensor 14, which contributes to the actuation of a new pusher 11; the latter transfers the conveying devices 5 from the shelf 10 of the apparatus to the peripheral unit 8b, from which they are then routed along the secondary lane 7 and then the main lane 6 of the automation system 3 that is located in the room on the upper floor (FIG. 5).

At the same time, on the opposite branch of apparatus 1, contrary operations take place for transferring the conveying devices 5 from the automation system 3 on the upper floor to the automation system 2 on the lower floor.

Figure 6:
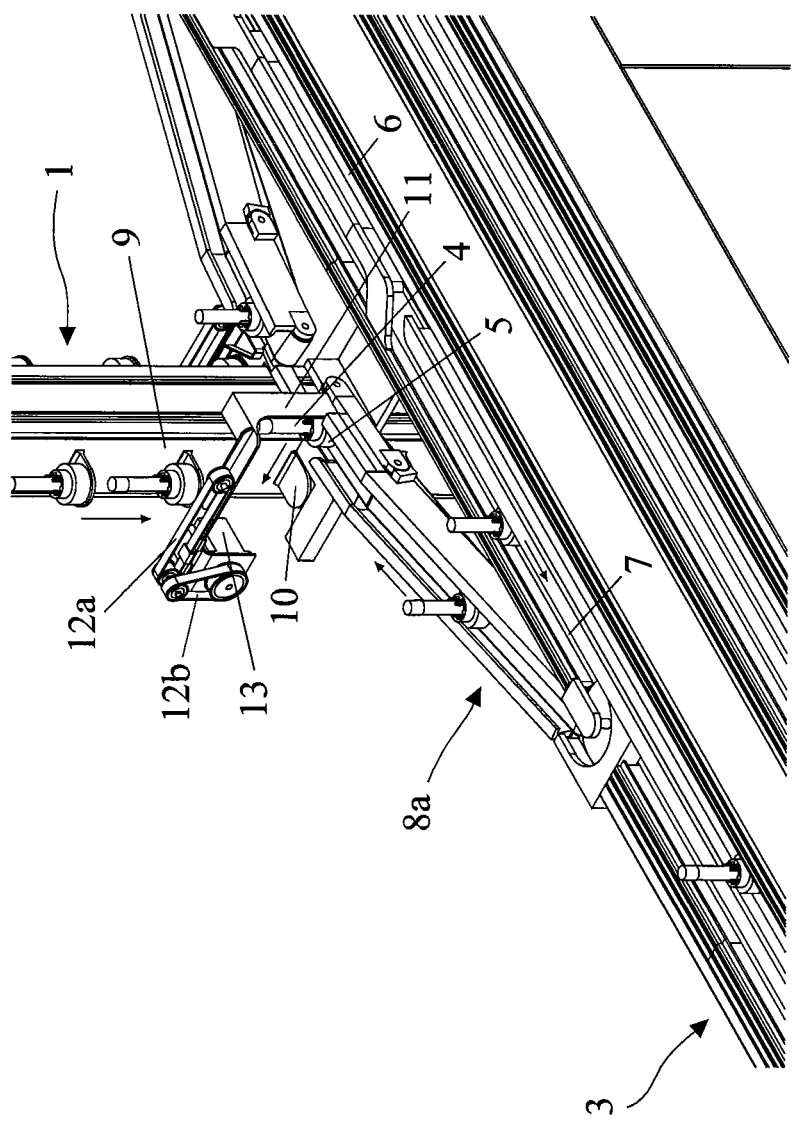
FIG. 6 shows a perspective view of a detail of the step of loading specimens from the automation system, placed at a higher height, to the apparatus.
Figure 7:
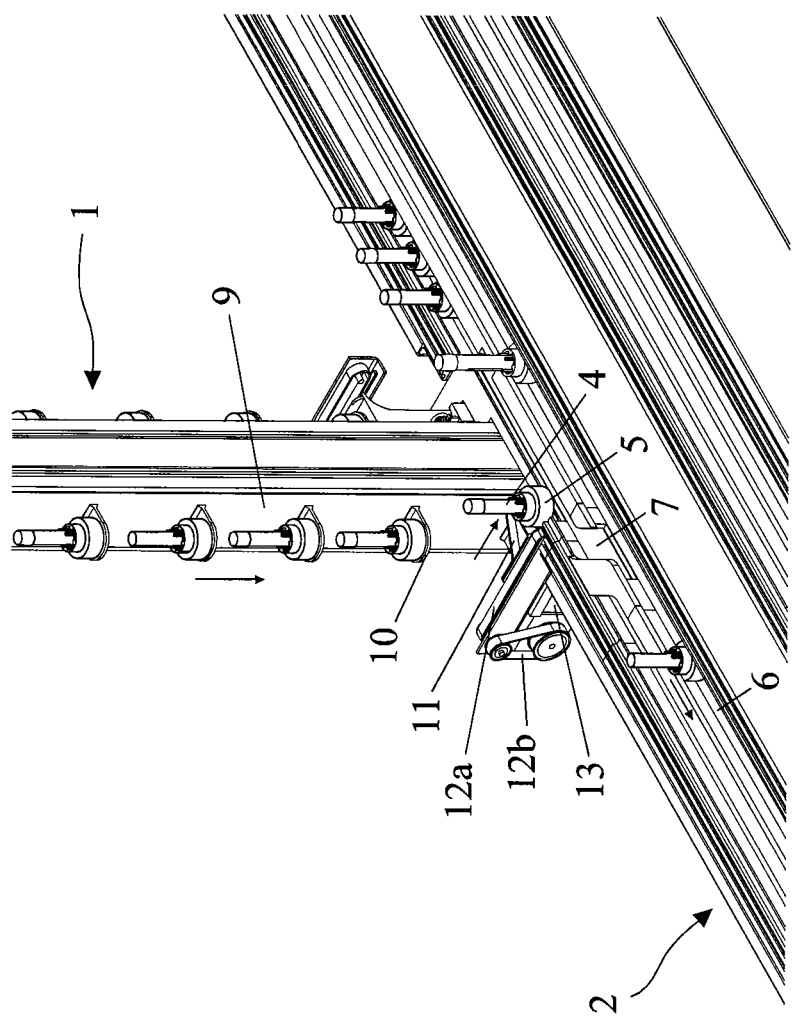
FIG. 7 shows a perspective view of a detail of the step of unloading specimens from the apparatus to the automation system placed at a lower height.

The conveying devices 5 are then appropriately diverted from the main lane 6 to the secondary lane 7 of system 3 and after crossing the peripheral unit 8a are pushed by a new pusher 11 within apparatus 1 (FIG. 6). Once at the base of apparatus 1, they are again pushed by another pusher 11 and directed along the secondary lane 7, and then along the main lane 6 of the automation system 2 on the lower floor (FIG. 7).

Therefore, it is the innovative aspect of the invention to ensure a complete automation of the process of transferring specimens between two or more different automation systems located on different floors at different heights, and in particular in separate rooms of a laboratory. Thereby, the laboratory operator is relieved from the manual performance of this task.

Moreover, the complete continuity and bidirectionality of such a transfer is ensured at any time. The apparatus of the invention in fact allows parallelizing the operations along its two distinct branches (an ascent branch and a descent branch), thereby also carrying out the transfer of specimens, from the automation system located at a lower level to that placed at a higher level and vice versa.

Moreover, since such an apparatus is essentially a monolithic block, any maintenance thereof is also quite simple.

Several changes and variations may be made to the invention thus conceived, all falling within the scope of the inventive concept.

In the practice, the materials used as well as the shapes and sizes may be any, according to the requirements.

The invention claimed is:

1. An analysis laboratory comprising at least a first and a second laboratory automation system, placed at different heights, and an apparatus for the transfer of conveying devices for single test tubes containing biological material, at least between said first and said second laboratory automation system, said conveying devices being adapted to keep said single test tubes in a vertical position during handling, said apparatus comprising a motor-driven belt, arranged vertically with respect to said first and second laboratory automation systems, shelves fixed to said motor-driven belt for accommodating said conveying devices, said shelves remaining horizontal during said transfer so that the test single tubes remain in vertical position, and pushers horizontally moving the conveying devices so as to keep the single test tubes in vertical position during the transfer from each of said first and second laboratory automation system to one of said shelves and vice versa, wherein each of said first and second laboratory automation system is provided with a main lane and a secondary lane, said shelves being fixed to said belt so as to face the secondary lane of each of the first and the second laboratory automation system, said pushers move said conveying devices from the secondary lane of each of the first and the second laboratory automation system to said shelves and vice-versa, and said belt allowing the conveying devices to be lifted from the first automation system to the second automation system, and the conveying devices to be simultaneously descended from the second automation system to first automation system.

2. The analysis laboratory according to claim 1, wherein the apparatus comprises a sensor able to detect the presence of said conveying devices and to actuate at least one of said pushers to move at least one of said conveying devices from said secondary lane of each of the first and the second laboratory automation system to one of said shelves and vice-versa.

3. The analysis laboratory according to claim 1, wherein the apparatus comprises a sliding system provided with a pair of belts driven by a motor to actuate at least one of said pushers.

4. The analysis laboratory according to claim 1, wherein the connection between said secondary lane of each of the first and the second laboratory automation system and said shelves is made by peripheral units with a ramp section, said peripheral units having a horizontal section at the transfer zone adjacent to said belt.

5. The analysis laboratory according to claim 1, wherein said first and second laboratory automation systems are placed in two separate rooms and said analysis laboratory comprises a cavity in a ceiling which separates said rooms, said cavity being protected by a layer of insulating and fire-retardant material.

* * * * *